Figure 1:
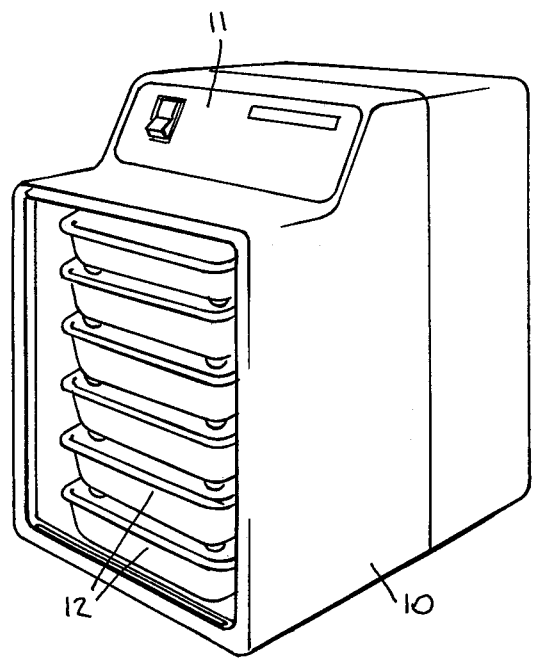

United States Patent [19]
Guibert

[11] 4,327,279
[45] Apr. 27, 1982

[54] COUNTER-TOP REHEATING UNIT FOR PACKAGED PRE-COOKED MEALS

[75] Inventor: Raul Guibert, Los Angeles, Calif.

[73] Assignee: Sunsetl, Ltd., Los Angeles, Calif.

[21] Appl. No.: 221,208

[22] Filed: Dec. 30, 1980

Related U.S. Application Data

[63] Continuation-in-part of Ser. No. 97,787, Nov. 27, 1979.

[51] Int. Cl.$^3$ .................... A21B 1/22; F27D 11/02
[52] U.S. Cl. .................... 219/400; 126/21 A; 126/110 A; 99/447; 99/355; 219/371; 219/385; 312/236
[58] Field of Search ............ 219/369, 370, 371, 385, 219/386, 388, 400, 533; 126/121 A, 261, 285 B, 110 A, 246; 99/355, 426, 447, 448, 480, 483; 206/499; 220/DIG. 13; 312/236

[56] References Cited

U.S. PATENT DOCUMENTS

| | | | |
|---|---|---|---|
| 3,526,752 | 9/1970 | Bell | 219/388 |
| 3,836,220 | 9/1974 | Ishammar | 312/236 |
| 3,861,378 | 1/1975 | Rhoadas et al. | 126/21 A |
| 4,030,476 | 6/1977 | Hock | 126/246 |
| 4,089,322 | 5/1978 | Guibert | 126/261 |
| 4,112,916 | 9/1978 | Guibert | 126/261 |
| 4,132,216 | 1/1979 | Guibert | 219/400 X |

FOREIGN PATENT DOCUMENTS

24389 12/1962 Fed. Rep. of Germany ...... 219/400

Primary Examiner—Volodymyr Y. Mayewsky
Attorney, Agent, or Firm—Michael Ebert

[57] ABSTRACT

A counter-top reheating unit for packages containing pre-cooked meals which are initially in a frozen state, the unit acting to quickly raise the temperature of the meals to a service temperature level and to maintain the meals at this level for an indefinite period. The unit includes a box-like case having telescoped therein an open-fronted inner box whose walls are spaced from those of the case to define rear and side air spaces therebetween. Mounted within the inner box is a compartment to receive a stack of packages with spacings therebetween. The perforated wall of the compartment is spaced from the rear of the inner box to define a rear plenum. In the heat-up phase, air in the rear space heated by both a high wattage and a low wattage heater element to a temperature well above the service level is blown into the plenum, the resultant pressure differential between the plenum and the rear space causing the air to flow at high velocity through the package spacings in the compartment and via the side spaces back to the rear space to create a continuous flow loop. The operation of the high wattage element is interrupted periodically whereby the meals are subjected to pulses of very hot air separated by lower-temperature intervals during which heat from the outer layer of the food is transferred into the body thereof to prevent the meals from being heated above the service temperature. In the subsequent service phase, the high-wattage element is cut off, and the temperature of the heated air is held at about the service level by the low-wattage element.

6 Claims, 5 Drawing Figures

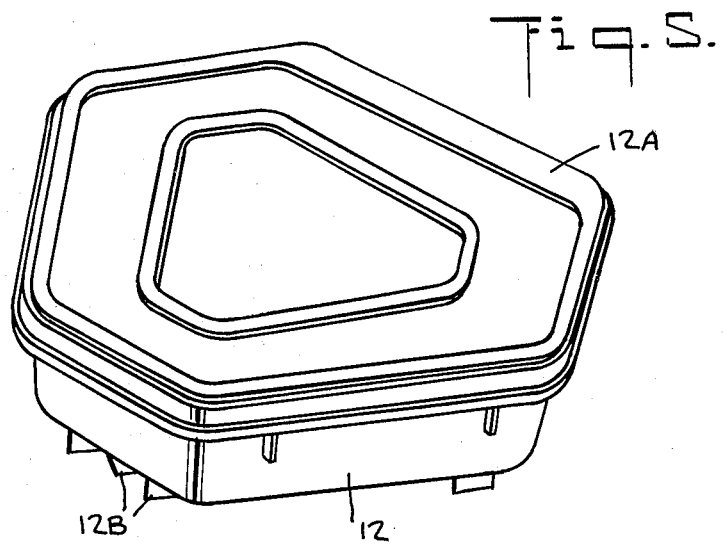
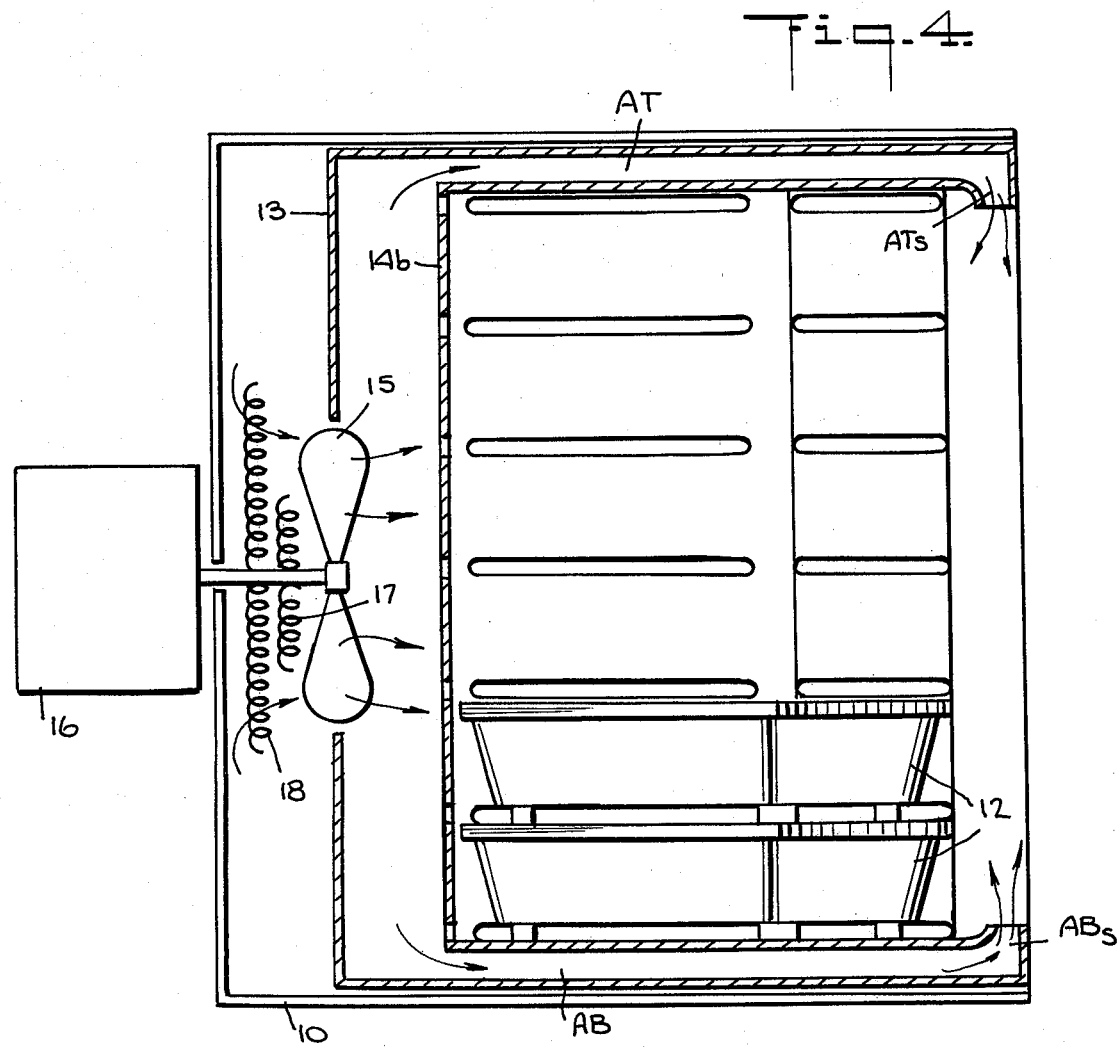

COUNTER-TOP REHEATING UNIT FOR PACKAGED PRE-COOKED MEALS

RELATED APPLICATION

This application is a continuation-in-part of my co-pending application Ser. No. 097,787, filed Nov. 27, 1979 entitled "Pulsating Hot-Air Heat-Up System."

BACKGROUND OF INVENTION

This invention relates generally to hot-air ovens for reheating packages containing pre-cooked meals initially in a frozen state, and more particularly to a counter-top unit of this type which is useable in homes and offices and is adapted rapidly to reheat a group of packages to a service temperature level and to maintain the meals at this level for an indefinite period.

To satisfy the growing need for quickly prepared inexpensive meals, convenience food systems have been developed in which the meals to be served at a later time are first cooked and packaged, and then deep-freezed. When one wishes to eat a particular meal, the selected package is taken out of the freezer and the frozen pre-cooked meal is then thawed and reheated. Typical of such operations is the so-called TV dinner in which a pre-cooked meal in the frozen state is sealed within a serving tray, the dinner being kept in the freezer until there is a demand for it, at which point the TV dinner is thawed and reheated in a microwave oven, a convection oven or whatever heater is available.

The term "packages" as used herein is intended to cover any sealed dish, tray or other container having a pre-cooked meal therein.

In reheating a pre-cooked frozen meal in homes and offices, it is difficult with conventional hot air ovens, when going from the frozen state to a service level, to avoid a situation in which the core of the meal is still cold even though the outer layer is quite hot. When one seeks to ensure that the body of the food is hot throughout, there is a tendency to overheat the meal and thereby re-cook it, with a resultant loss in nutritional value and flavor. And assuming that the meal has been heated to a proper serving level, it must be served without delay, for with the typical oven it is virtually impossible to thereafter hold the meal in the oven until such time as there is a demand therefor without overheating.

A microwave oven has the advantage of reheating a pre-cooked meal from the inside out, rather than the other way around. But since microwave heating depends on the dielectric properties of the body being heated and no two pre-cooked frozen meals have the same characteristics in this regard, the results of microwave heating are highly variable. Moreover, once the pre-cooked meal is heated in a microwave oven, it cannot be maintained in a heated condition and must be served shortly thereafter.

For a convenience food operation to be effective, one must be able not only to reheat the pre-cooked meal to a proper service temperature level within a relatively short time, but one must be able to take into account the fact that in a home and office, the time at which diners are ready to eat may be subject to change. Thus in a typical office having several staff members, all of whom intend to lunch at say noon, it is not at all unusual for one or more of the members to be unavailable until say an hour or so later. Existing ovens for reheating pre-cooked frozen meals cannot cope with this common contingency.

My prior U.S. Pat. No. 4,112,916, "Hot Air Oven for Food-Loaded Cartridges" discloses a fast food service technique in which pre-cooked food which has been refrigerated may thereafter be reheated and made directly available to diners without degrading the essential texture, flavor or nutritional qualities of the meal.

In this patent, a hot air oven is provided for heating tray-loaded cartridges, each constituted by a stack of sealed trays containing pre-cooked meals nested within an open carton whose side walls have holes therein to admit heated air. The oven includes a rotating turntable provided with a raised annular shelf for supporting an annular array of cartridges, the side walls of which define a hollow center core.

A heater assembly above the annular cartridge array produces heated air which is blown into the hollow core. Because of the flow restriction, a substantial portion of the heated air is forced through the holes of the cartons to heat the food in the trays. The remaining portion of the heated air passes through the flow passage, the air discharged from the outlet thereof being drawn upwardly by suction force to create an air curtain around the cartridge array.

In an oven of the type disclosed in my prior patent, a two-section heating assembly is provided having different wattages, whereby at the outset of heating, both sections are operative for a controllable period, hereinafter called the heat-up phase, sufficient to raise the food temperature to the desired service level, after which the main section is rendered inactive while the thermostatically-controlled auxiliary section, which draws much less power, then serves to maintain indefinitely the heated food at the proper level for service to diners, hereinafter called the "service phase."

During the heat-up phase, the rate of heat transfer from the hot air in the oven to the cold food-loaded cartridges depends on the temperature differential; the greater the difference between the hot air temperature and the food temperature, the more rapid the rate of heat transfer. Since the hot-air temperature throughout the oven is at a fairly uniform level, the transfer rate at the outset of the heat-up phase, when both heater sections are operative, is very rapid. But as the difference in temperature between the hot air and the food thereafter diminishes, the rate of transfer becomes increasingly slow as the service temperature is approached.

Assuming that the food in the cartridges is initially at a temperature of about 10° F. and it is necessary to raise the food temperature to a service level of about 150° F., and further assuming a hot air temperature of about 165° F., then at the outset of the heat-up phase, there will be a sharp differential giving rise to very rapid heating. But as this temperature differential diminishes in the course of the heat-up phase, the rate of heat transfer slows down considerably. When, for example, the food temperature reaches 130° F., the temperature differential relative to the heated air is only 35° F., and it takes a relatively long time before the food temperature can be raised to the service temperature of 150° F., at which point the heat-up phase is concluded and the service phase takes over with only one heater section operative to maintain this service temperature level.

Similarly, in convection-heating units of the type heretofore available commercially, one can set the oven for a desired heat-up temperature. But as previously explained, the temperature differential between the cold food and the heated air is large only in the initial heat-up period, and the closer the food approaches the service temperature, the smaller the differential and the more sluggish the rate of heat transfer. Consequently, it takes an unacceptably long time for the food to reach the service temperature. This is particularly the case when the unit is fully loaded with several trays or packages of frozen food.

If the operator of a standard oven tries to accelerate the heat-up phase by setting the temperature level of the oven well above the service temperature, the resultant heating will generally be destructive of the food; for the outer layers of the body of food will then be heated to an excessive level, causing these layers to be re-cooked or burned while the intermediate layers and the core of the body are still well below the service temperature level.

In my above-identified copending application, there is disclosed an oven adapted to rapidly raise the temperature of pre-cooked meals from the cold or frozen state to a service temperature level at which the meal is in condition to be service, and to maintain the meal at this level until there is a demand therefor. This oven is provided a thermally-insulated chamber having a fluid-permeable receiving compartment flanked by input and output plenums.

A main flow loop is provided in which the chamber is connected in a continuous flow path in series with a heater station and an air pump or blower in an arrangement in which air drawn via an output line from the output plenum and creating a negative pressure therein is conducted through the heater station and then forced in the heated state through an input line leading into the input plenum to create a positive pressure therein. The resultant pressure differential between the plenum causes heated air to flow at high velocity through the compartment to heat the meals contained therein.

A by-pass extending between the input to the heater station and the junction of the chamber and the pump in the main flow loop defines a feedback flow loop which excludes the chamber. A damper mechanism at this junction is cyclically driven to periodically block the flow of heated air through the main loop into the chamber and to divert the flow into the feedback loop for recirculation therein.

As a consequence, main loop flow through the chamber assumes the form of a pulsatory wave whose fluidic pulses have a peak temperature whose level is well above the predetermined temperature level and whose relaxation periods are at a temperature below this predetermined level, thereby promoting rapid heat transfer in the body of the pre-cooked meal without, however, raising the surface temperature thereof above this level. This action is continued until the entire body of the meal is at the desired service temperature level, at which point the system is operated to maintain this level indefinitely without overheating the meal.

SUMMARY OF INVENTION

In view of the foregoing, the main object of this invention is to provide a counter-top unit useable in homes and offices for reheating a group of packages containing pre-cooked meals so that they are brought from the frozen state to a service temperature level in a relatively short period and thereafter maintained indifinitely at this level.

More particularly, it is an object of this invention to provide a unit which is especially adapted to reheat a stack of sealed hexagonally-shaped trays containing pre-cooked meals.

Yet another object of the invention is to provide a unit of the above-type which is highly compact and which may be manufactured at low cost.

A significant advantage of a unit of the above-type is that it makes it possible in an office or similar facility to store a variety of packages containing pre-cooked meals in a freezer, such as fish, meat or vegetable-based meals, and to select from this inventory a group of different meals to be served. The selected packages are transferred to the unit which is turned on about an hour before the lunch or dinner hour so that it is then ready to be served in that hour or at a later period should any diner be delayed for any reason. Since the reheating of the meals does not result in recooking thereof, should a reheated meal not be eaten, it may be returned to the freezer for subsequent use.

Briefly stated, these objects are accomplished in a counter-top reheating unit for packages containing pre-cooked meals which are initially in a frozen state, the unit acting to quickly raise the temperature of the meals to a service temperature level and to maintain the meals at this level for an indefinite period. The unit includes a box-like case having telescoped therein an open-fronted inner box whose walls are spaced from those of the case to define rear and side air spaces therebetween. Mounted within the inner box is a compartment to receive a stack of packages with spacings therebetween. The perforated wall of the compartment is spaced from the rear of the inner box to define a rear plenum. In the heat-up phase, air in the rear space heated to a temperature well above the service level is blown into the plenum, the resultant pressure differential between the plenum and the rear space causing the air to flow at high velocity through the package spacings in the compartment back to the rear space to create a continuous flow loop.

Heat is provided by high-wattage and low-wattage heater elements, both of which are energized in the heat-up phase to provide the required high temperature. However, in the heat-up phase, the operation of the high-wattage element is periodically interrupted whereby the meals are then subjected to pulses of high-temperature air separated by relatively low-temperature intervals during which heat from the outer layer of the food is transferred to the intermediate layers and the core thereof to prevent the outer layer from being heated above the service temperature.

When the body of the meals reach the service temperature, the unit switches over to a service phase in which only the low-wattage heater element is energized and thermostatically-controlled to maintain the food at the service temperature level for an indefinite period.

OUTLINE OF THE DRAWINGS

Figure 3:
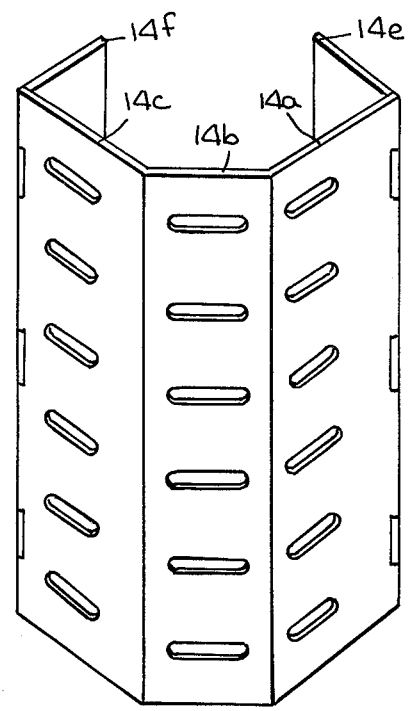
Figure 2:
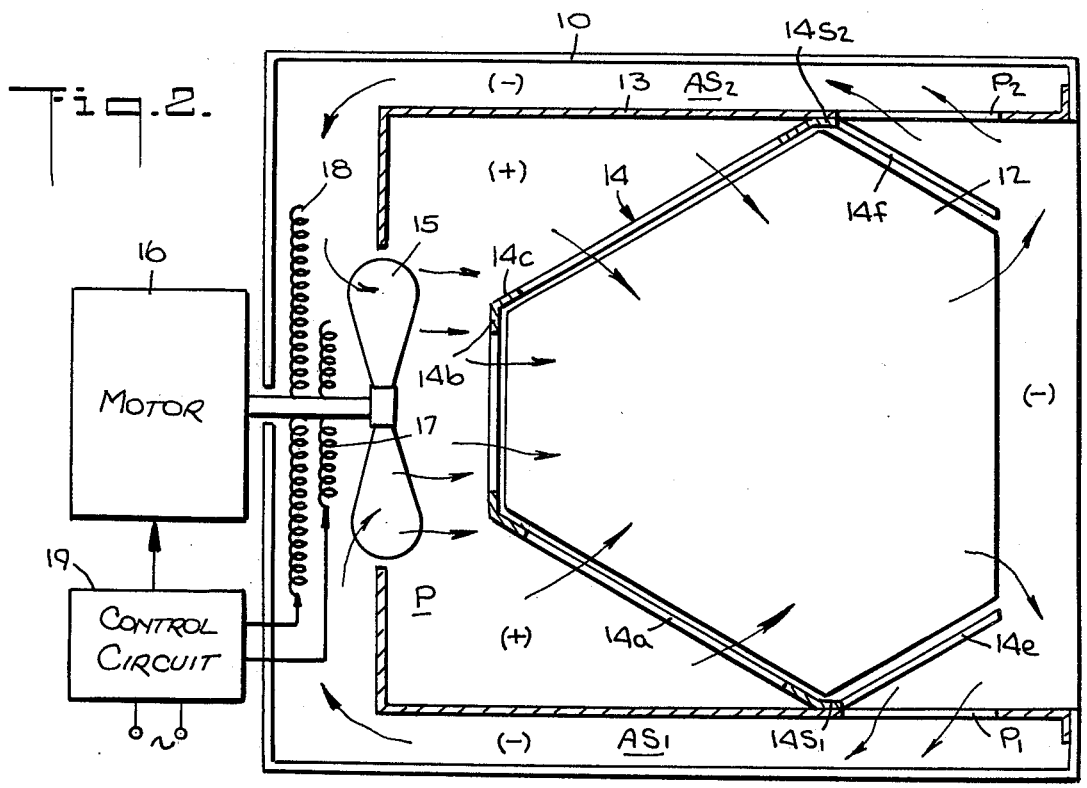

For a better understanding of the invention as well as other objects and further features thereof, reference is made to the following detailed description to be read in conjunction with the accompanying drawings wherein:

FIG. 1 is a perspective view of a heat-up unit in accordance with the invention;

FIG. 2 schematically shows the unit in a section taken horizontally therethrough;

FIG. 3 schematically shows the unit in a section taken vertically therethrough;

FIG. 4 is a separate perspective view of the compartment included in the unit; and FIG. 5 is a separate perspective view of one of the sealed trays containing a pre-cooked meal.

DESCRIPTION OF INVENTION

Structure of Unit

Referring now to FIG. 1, a unit in accordance with the invention for reheating a stack of packages containing frozen pre-cooked meals includes a box-like case 10 having an open front. The case further includes an upper section adapted to house control devices and including a control panel 11 on which there are mounted switches, indicators and other control elements.

In practice, the unit may be provided with a front door to close the unit except when food packages are being loaded therein or withdrawn. But because the unit, as will later be evident, generates a front air curtain which thermally isolates the food packages from the exterior atomsphere, a door is not an essential component thereof. In the absence of a door, one has immediate access to the interior of the unit.

The unit is loaded with a stack of six trays 12 of identical hexagonal shapes, each tray having three angled back sides and three angled front sides. The trays all contain pre-cooked meals in the frozen state, the trays having been taken from a storage freezer and put in the unit about an hour before the scheduled meal-time to allow for adequate heat-up.

In practice, each tray may carry an identifying front label, so that if six different meals are to be served, these will be indicated on the trays. And if for some reason, one or more trays is left over after meal time, they may be returned to the freezer for subsequent reheating. The unit acts only to reheat and does not recook or otherwise impair the quality of the meals, hence repeated reheatings and refreezings can be tolerated within practical limits.

As shown separately in FIG. 5, each tray 12 is provided with a removable lid 12A which seals the contents, the lid being peeled off after the tray has been taken from the unit. Tray 12 also includes spacer element 12B so that when the trays are stacked in the unit, air spacings exist therebetween to admit hot air in the manner to be later explained. A more detailed description of the hexagonal trays and the advantages thereof may be found in the related applications referred to in the above-identified copending application of which the present case is a continuation-in-part.

As best seen in FIGS. 2 and 3, an inner box 13 of smaller dimensions is supported within case 10, the inner box also having an open front. The front edges of the sides of the inner box are joined by bridging panels to the corresponding sides of the case.

A compartment 14 adapted to accommodate the stack of trays 12 is disposed within inner box 13 and attached at an intermediate point to the side walls thereof by vertical strips $14S_1$ and $14S_2$. Compartment 14, as shown separately in FIG. 4, has three angled side walls $14a$, $14b$ and $14c$ with ventilation holes thereon, the angles of these sides corresponding to those of the back sides of the trays received in the compartment. Thus the trays nest neatly within the compartment.

Compartment 14 is provided with front flaps $14e$ and $14f$ which are hinged to the edges of side walls $14a$ and $14c$, respectively. These hinged flaps are spring-biased to urge the flaps inwardly against the corresponding front sides of the trays. In order therefore to load the compartment or to remove trays therefrom, the flaps must first be swung out. When released, the flaps return to their normal position.

Compartment 14 is positioned within inner box 13 so as to form therewith a rear plenum P. As shown in FIG. 2, the spaces between the sidewalls of the inner box and those of the case define side air spaces $AS_1$ and $AS_2$ which communicates with a rear air space AR seated between the rear of the inner box and the case. Top and bottom air spaces AT and AB formed between the top and bottom walls of the inner box and the top and bottom of the case communicates with plenum P, as best seen in FIG. 3.

Disposed within a central port in the rear wall of inner box 13 is a propeller fan 15 driven by a motor 16. This motor may be placed in the upper section 11 of the case and coupled by a suitable gear train to the propeller, or it may be placed in rear air space AR, in which event it must be capable of operating in a high temperature environment.

Disposed within rear space AR are two electrical resistance heater elements 17 and 18 having different wattage ratings, one being a low-wattage element (i.e., 300 watts), and the other a high-wattage element (i.e., 1000 watts). These elements, as well as motor 16, are operated through a control circuit 19 which includes a timer and other control means to turn on the fan and selectively energize the resistance elements in accordance with the operating program of the unit.

OPERATION OF UNIT

When fan 15 is operated and heaters 18 and 19 are both energized, the air in rear space AR is heated to a high temperature well above the service temperature level of the meals, say, to 400° F. The hot air is blown by the fan into plenum P. As a consequence, the air in plenum P is under positive pressure, whereas the air in rear air space $AR_1$ and in side air spaces $AS_1$ and $AS_2$ are under negative pressure. The side air spaces communicate with the front of compartment 14 through side ports $P_1$ and $P_2$.

This gives rise to a pressure differential causing hot air to be projected through the holes in walls $14a$, $14b$ and $14c$ of the compartment and to flow at high velocity through the spacings between the trays in the stack. This high velocity flow results in the rapid transfer of heat from the hot air stream to the cold food in the trays. The air emerging from the front of compartment 14 which has lost heat in the course of transit is drawn back to rear air spaces AR through side air spaces $AS_1$ and $AS_2$ where the air is again heated before being blown back into plenum P. Thus a continuous flow loop is created which recirculates hot air through the compartment in heat exchange relationship with the trays therein.

At the same time, hot air under positive pressure is forced from plenum P through the top and bottom air spaces AT and AB, the air from these spaces being discharged through slots $AT_s$ and $AB_s$ over the open front of the compartment to form an air curtain thereacross which thermally isolates the compartment from the exterior so that even though the compartment is open, there are no significant heat losses.

If hot air flow in the unit were uninterrupted, because the temperature thereof is much above the service level, the outer layer of the food would, in short order, heat up to a point resulting in recooking or scorching of the meal, whereas the intermediate layers and the core would still lie below the service temperature.

In order, therefore, to rapidly heat up the pre-cooked meals to a level not in excess of the service temperature and to bring about a uniform distribution of heat in the food body, in a unit in accordance with the invention when operating in a heat-up phase, the energization of the high-wattage heater element is periodically interrupted, whereas energization of the low-wattage element is continuous to produce very hot air pulses separated by relatively low-temperature intervals. To this end, control circuit 19 functions by means of a motorized switching mechanism or equivalent electronic means to turn high-wattage heater element 18 "on" and "off" periodically, say, 30 seconds "on" and 30 seconds "off" in the course of each operating cycle during the heat-up phase.

In this way, even though the temperature of the hot air pulses is very high, because during the low-temperature intervals heat is transferred from the outer layer of the food body to the intermediate layer and from there to the core of the body, this brings about a reduction in the temperature of the outer layer which prevents excessive heat-up thereof.

And because of the great heat differential between the hot air pulses and the outer food layer, rapid heat transfer takes place therebetween during the pulse periods even as the temperature of the outer layer approaches the service temperature level; for at this level there is still a large heat differential.

Thus it becomes possible with pulsatory wave heating during the heat-up phase to rapidly heat up the meals in the trays in a relatively short period; i.e., an hour or less. The control circuit includes a timer that is pre-set so that upon completion of the heat-up phase, the system is switched over to operate continuously with only the low wattage heater "on" which is thermostatically governed to maintain the interior temperature of the unit at the service temperature for an indefinite period. A light indicator on the control panel is energized when the unit switches over to the service phase, thereby indicating that the meals may be dispensed to diners.

While there has been shown and described a preferred embodiment of a counter-top reheating unit for packaged pre-cooked meals in accordance with the invention, it will be appreciated that many changes and modifications may be made therein without, however, departing from the essential spirit thereof.

Thus while the geometry of compartment 14 in the unit is designed to accommodate hexagonally-shaped trays, it may be configured to nest trays or packages having other shapes, such as round or rectangular trays.

I claim:

1. A counter-top reheating unit for packages containing pre-cooked meals, the unit being adapted to quickly raise the temperature of the meals to a service temperature level that is below the temperature at which cooking takes place, said unit comprising:
   A. a box-like case having an inner box nested therein, said case and said box having an open front; the dimensions of the inner box relative to the case being such as to define a rear air space and side air spaces communicating therewith;
   B. a compartment for accommodating a stack of said packages with spacings therebetween, said compartment fitting within the inner box and having a perforated rear wall spaced from the rear of the inner box to define therewith a plenum, said compartment having a front air space leading to said side air spaces; and
   C. means to heat the air in the rear air space to a temperature well above the service temperature level and to blow the resultant hot air into said plenum to create a positive pressure therein, thereby developing a negative pressure in said air spaces, the resultant pressure differential forcing the hot air through said perforated wall and causing the hot air to flow at high velocity through said package spacings in heat exchange relationship with said pre-cooked meals, the hot air then passing from the front air space into said side air spaces and back to said rear air space to create a flow loop recirculating the hot air through said compartment.

2. A unit as set forth in claim 1, wherein said air is heated by low and high-wattage heater elements both of which are energized in said heat-up phase, only one of which is energized in a subsequent service phase which acts to maintain the meals at the service temperature, the high wattage element in the heat-up phase being periodically interrupted to subject the packages to very hot air pulses separated by relatively low-temperature intervals during which heat is transferred from the outer layer of the meals to the intermediate layers and the core thereof, the resultant reduction in the temperature of the outer layer preventing this layer from reaching a temperature above the service level.

3. A unit as set forth in claim 1, further including top and bottom air spaces between the inner box and the compartment which communicate with the plenum whereby hot air under positive pressure is forced through these spaces and discharged across the front space to create an air curtain preventing the loss of heat.

4. A unit as set forth in claim 1, wherein said packages are sealed trays having a hexagonal form.

5. A unit as set forth in claim 4, wherein said compartment is composed of three angled walls having holes therein, said walls corresponding to the three back sides of the trays.

6. A unit as set forth in claim 5, wherein said compartment further includes spring-biased flaps hinged to the side walls of the compartment.

* * * * *